United States Patent [19]

Sakharova

[11] Patent Number: 4,826,682

[45] Date of Patent: May 2, 1989

[54] BAIT COMPOSITION AND INSECTICIDE

[76] Inventor: Bronislava Sakharova, 605 Washington St., Peekskill, N.Y. 10566

[21] Appl. No.: 33,837

[22] Filed: Apr. 3, 1987

[51] Int. Cl.$^4$ ............... A01N 59/06; A01N 59/14; A01N 59/18; A01N 59/22

[52] U.S. Cl. ............... 424/623; 424/84; 424/645; 424/659; 424/685

[58] Field of Search ............... 424/84, 133, 146, 148, 424/154

[56] References Cited

U.S. PATENT DOCUMENTS

| | | | |
|---|---|---|---|
| 890,636 | 6/1908 | Fride | 424/148 |
| 1,082,507 | 12/1913 | Ellis et al. | 424/146 |
| 1,450,128 | 3/1923 | Baker | 424/133 |

FOREIGN PATENT DOCUMENTS

| | | | |
|---|---|---|---|
| 2408001 | 8/1975 | Fed. Rep. of Germany | 424/148 |
| 57-203061 | 12/1982 | Japan | 424/148 |
| 58-52205 | 3/1983 | Japan | 424/148 |

OTHER PUBLICATIONS

Abstract of Japanese Patent J58121-203-A (7/19/83).
Hocking; A Dictionary of Terms in Pharmacognosy and other Divisions of Economic Botany; pp. 64 & 179.

*Primary Examiner*—Allen J. Robinson
*Attorney, Agent, or Firm*—Rodman & Rodman

[57] ABSTRACT

The present invention relates to a bait composition for insects comprising a mixture of cucumbers, eggs, potatoes, sugar and honey. The bait composition can incorporate an insecticidal mixture of boric acid, mercuric chloride, arsenic trioxide and aluminum sulfate.

11 Claims, No Drawings

BAIT COMPOSITION AND INSECTICIDE

BACKGROUND OF THE INVENTION

1. Field of the Invention

This invention relates to an insect bait composition, and more specifically toan insect bait composition incorporating an insecticide.

2. Description of the Prior Art

The cockroach is among the oldest insect pests known to mankind. Millions of dollars are spent each year by Americans seeking to rid themselves of cockroaches and other insects. The 1986 insecticide market has been estimated to be about $550 million in the United States, and includes scores of products, most of which are intended for cockroaches. These products include traps containing glue, poisonous powders and sprays as well as compounds designed to control the reproductive cycle of the roach.

Literally hundreds of methods have been developed in attempts to rid the home and workplace of the cockroach. However, none of these methods have worked effectively for extensive periods of time. This is due to the fact that cockroaches demonstrate a unique ability to adapt to practically any means for keeping them in check.

Roaches breed at a high rate and, accordingly, complete eradication of this noxious pest is quite difficult. Nevertheless, effective control has been accomplished using various methods such as residual insecticide sprays, and the placing of cockroach bait compositions containing insecticides in suitable locations.

Residual sprays, although effective for a reasonable length of time on many surfaces are not effective on all surfaces. For example, a residual spray that is effective on a non-porous surface, such as stainless steel or sealed ceramic tile, may not be effective when used on a porous of surface, such as unpainted wood or unsealed tile.

Prior art bait compositions include dog food, oatmeal, corn syrup, corn husks or grain, and the like.

U.S. Pat. No. 4,049,960 to Broadbent discloses a cockroach bait comprising a mixture of dry dog food, maltose, brown sugar and a binder such as wax, carboxymethyl cellulose or starch.

U.S. Pat. No. 4,617,188 to Page et al discloses the use of carob as an attractant to cockroaches. Corn starch is added to the carob, which is hygroscopic, to absorb moisture and serve as an anti-caking agent.

SUMMARY OF THE INVENTION

The present invention relates to a bait composition for insects comprising a mixture of cucumbers, eggs, potatoes, sugar and honey. The bait composition preferably incorporates an insecticidal mixture of boric acid, mercuric chloride, arsenic trioxide and aluminum sulfate. A process for preparing the insecticidal bait composition is also disclosed.

DESCRIPTION OF THE PREFERRED EMBODIMENTS

In accordance with the present invention, a bait composition to attract insects, such as cockroaches, includes an intimate mixture of the following components, in percent by weight:

|  | % |
| --- | --- |
| cucumbers | 10–50 |
| eggs | 2–20 |
| potatoes | 15–60 |
| sugar | 2–20 |
| honey | 2–20 |

The bait composition preferably includes an insecticidally effective composition for cockroaches, comprising an intimate mixture of the following components in percent by weight:

|  | % |
| --- | --- |
| boric acid | 15–50 |
| mercuric chloride | 5–25 |
| arsenic trioxide | 15–50 |
| aluminum sulfate | 15–50. |

Boric acid is a colorless, odorless, transparent crystal, or white granule or powder. It is slightly unctuous to the touch. Mercuric chloride comes in the form of crystals or white granules or powder. Arsenic trioxide has two crystalline modifications, claudetite (monoclinic, melting point 313° C.) and arsenolite (cubic, melting point 275° C.), and comes in the form of white or transparent, glassy, amorphous lumps or crystalline powder. Aluminum sulfate comes in the form of white, lustrous crystals, pieces, granules, or powder. The commercial product is also known as "alum".

Other insecticides can also be utilized as components of the insecticidal bait composition, such as hydramethylnon, the insecticide used in Combat ®, a roach killer marketed by Cyanamid Corp. Derivatives of phosphorodithioic acid and/or phosphorothioic acid, borax, boric acid, mercuric chloride, arsenic trioxide and aluminum sulfate, individually, or in mixtures can also be utilized as insecticide components.

The insecticidal bait composition can also include insect growth regulators, such as hydroprene, which induces homosexuality among the American cockroach, but not the German cockroach.

Generally, the amount of the insecticide can vary from about 5 to 30% by weight of the total insecticidal bait composition, which includes other suitable optional additives.

It has been found that the cucumber component is suitably prepared for inclusion in the bair composition by cutting or chopping the cucumber into finely divided particles which can vary in weight from about 0.05 to 0.5 grams.

The potato component can be suitably prepared for inclusion in the bait composition by boiling until the potatoes becomes soft, followed by mashing or grinding into finely divided particles or a puree. The particles can range from about 0.05 to 0.5 grams.

The egg component can be suitably prepared by hard boiling the eggs. The eggs are then chopped or ground into finely divided particles ranging from about 0.05 to about 0.5 grams.

The sugar component is suitably in granulated form with a particle size typical of the sugars sold in any supermarket for domestic use. White sugar or brown sugar can be used, but white sugar is preferred purely for economical reasons.

The honey component is of the type commonly found in most supermarkets for domestic use. No special preparation is necessary.

The cucumber component can be chopped or ground up into finely divided particles.

Although the bait components can be mixed in any particular order, it is preferred that the bait composition be prepared by first mixing the potatoes and eggs, then adding and mixing the cucumbers, sugar and honey until a uniform mixture is obtained.

The insecticide components can be separately prepared and mixed with the bait components to produce a uniform homogeneous insecticidal bait composition.

The bait composition has been found to be particularly effective in attracting cockroaches. The consistency of the bait composition is initially that of a tacky, unctuous material which over a period of time will dry to a non-unctuous state.

A cockroach or other insect will be attracted by the bait, eat the composition and then expire.

It has been found that the insecticidal bait composition will not immediately dispatch the cockroach. Rather, the killing effect is delayed, which is preferable because it works against the cockroaches' instincts as well as its physiology. Thus, since the insecticidal bait composition does not kill the cockroach immediately, the insect does not learn to avoid it.

The insecticidal bait composition can be formed into a variety of shaped objects of different sizes suitable for placing in various locations inhabited by cockroaches. The physical shape and size of the insecticidal bait composition will depend upon such factors as the location of its deployment, and how it is deployed whether housed in a trap or other convenient accommodating structure, or simply distributed about in its neat form. The traps, known to the art, are desirable and convenient to prevent the access of small children and pets from accidentally ingesting the insecticidal bait composition. Suitable shapes can be spheres, elipsoids, and polygons weighing from about 2 to about 50 grams, but this is by no means exclusive.

EXAMPLE

A bait composition and insecticide were formed from the following components, finely divided and intimately admixed:

| Component | Approximate Weight (Grams) |
| --- | --- |
| cucumbers | 500 |
| eggs | 150 |
| potatoes | 600 |
| sugar | 150 |
| boric acid | 100 |
| mercuric chloride | 50 |
| arsenic trioxide | 100 |
| honey | 150 |
| aluminum sulfate | 100 |

The cucumbers were chopped on a conventional kitchen grating device. The eggs were hard boiled and chopped up. The potatoes were boiled until they were soft and were chopped up into finely divided particles. The sugar and honey were mixed and added to the cucumbers, potatoes and eggs, then combined with the boric acid, mercuric chloride, arsenic trioxide and aluminum sulfate to produce the insecticidal composition.

After the insecticidal composition was produced, small shaped portions weighing from about 5 to 10 grams were prepared and distributed in the kitchen, sink areas, stove areas, and in locations where the presence of cockroaches was noted, in an apartment in a multiple story apartment building having a cockroach problem. After about 7-10 days, the presence of the cockroaches were significantly reduced and shortly thereafter their presence ceased. After six months of continued usage of the insecticidal composition, there was no noticeable presence of cockroaches in spite of the fact that the apartment kitchen was located in an apartment building with a continuing cockroach problem.

The present invention can be implemented in other specific ways than those set forth herein without departing from the spirit and essential characteristics of the invention. The embodiments discussed herein, therefore, are to be considered in all respects as illustrative, and not restrictive.

What is claimed is:

1. An unctuous cohesive homogeneous insecticidal composition comprising an intimate mixture of the following bait components, in percent by weight:

| | % |
| --- | --- |
| cucumbers | 10-50 (finely divided) |
| whole, hard boiled eggs | 2-20 (finely divided) |
| boiled potatoes | 15-60 (finely divided) |
| sugar | 2-20 (finely divided) |
| honey | 2-20, | and an insecticidally effective amount of a mixture of the following insecticides, in percent by weight:

| | % |
| --- | --- |
| boric acid | 15-50 |
| mercuric chloride | 5-25 |
| arsenic trioxide | 15-50 |
| aluminum sulfate | 15-50 |

2. The composition of claim 1, wherein the amount of the insecticide varies from about 5 to 30% by weight of the total composition.

3. The composition of claim 1, in the form of shaped objects weighing from about 0.5 to about 100 grams.

4. The composition of claim 1, housed in a trap.

5. The composition of claim 1, wherein the insecticide is effective to kill cockroaches.

6. The composition of claim 1, wherein the insecticide is used indoors in the home or workplace.

7. A method for attracting and killing insects using an unctuous insecticidal composition comprising a homogeneous intimate mixture of the following bait components in percent by weight:

| | % |
| --- | --- |
| cucumbers | 10-50 (finely divided) |
| whole, hard boiled eggs | 2-20 (finely divided) |
| cooked potatoes | 15-60 (finely divided) |
| sugar | 2-20 (finely divided) |
| honey | 2-20, | and an insecticidally effective amount of a mixture of the following insecticides, in percent by weight:

|  | % |
| --- | --- |
| boric acid | 15-50 |
| mercuric chloride | 5-25 |
| arsenic trioxide | 15-50 |
| aluminum sulfate | 15-50 | and deploying said insecticidal bait composition in suitable locations in the form of small, cohesive shaped objects varying from about 0.5 to about 100 grams.

8. The method of claim 7, wherein the amount of the insecticide varies from about 5 to 30% by weight of the total composition.

9. The method of claim 7, wherein the insecticidal composition is housed in a trap.

10. The method of claim 7, wherein the insecticide is effective to kill cockroaches.

11. The method of claim 7, wherein the insecticide is used in the home or workplace.

* * * * *

UNITED STATES PATENT AND TRADEMARK OFFICE
CERTIFICATE OF CORRECTION

PATENT NO. : 4,826,682

DATED : May 2, 1989

INVENTOR(S) : Bronislava Sakharova

It is certified that error appears in the above-identified patent and that said Letters Patent is hereby corrected as shown below:

At column 2, line 51, change "bair" to --bait--.

At column 4, line 63, change "cooked" to --boiled--.

Signed and Sealed this

Sixteenth Day of January, 1990

*Attest:*

JEFFREY M. SAMUELS

*Attesting Officer*  *Acting Commissioner of Patents and Trademarks*